United States Patent [19]

Leyshon et al.

[11] Patent Number: 5,026,935
[45] Date of Patent: Jun. 25, 1991

[54] ENHANCED PRODUCTION OF ETHYLENE FROM HIGHER HYDROCARBONS

[75] Inventors: David W. Leyshon; John A. Sofranko, both of West Chester; C. Andrew Jones, Newtown Square, all of Pa.

[73] Assignee: Arco Chemical Technology, Inc., Wilmington, Del.

[21] Appl. No.: 415,506

[22] Filed: Oct. 2, 1989

[51] Int. Cl.$^5$ .............................................. C07C 4/06
[52] U.S. Cl. ...................................... 585/315; 585/324; 585/643; 585/644; 585/648; 585/650; 585/651; 585/653
[58] Field of Search ............... 585/315, 324, 643, 644, 585/648, 650, 651, 653

[56] References Cited

U.S. PATENT DOCUMENTS

| 3,431,316 | 3/1969 | Banks | 585/643 |
| 3,485,890 | 12/1969 | Dixon | 585/324 |
| 4,172,816 | 10/1979 | Pop et al. | 585/653 |
| 4,613,721 | 8/1986 | Kaiser | 585/650 |

FOREIGN PATENT DOCUMENTS 0109059 5/1984 European Pat. Off. .

Primary Examiner—Curtis R. Davis
Attorney, Agent, or Firm—William C. Long

[57] ABSTRACT

The present invention provides a process for the preparation of ethylene from $C_4$ or higher feed by a combination of cracking and metathesis wherein higher hydrocarbon is cracked to form ethylene and propylene and at least a portion of the propylene is metathesized to ethylene.

2 Claims, 2 Drawing Sheets

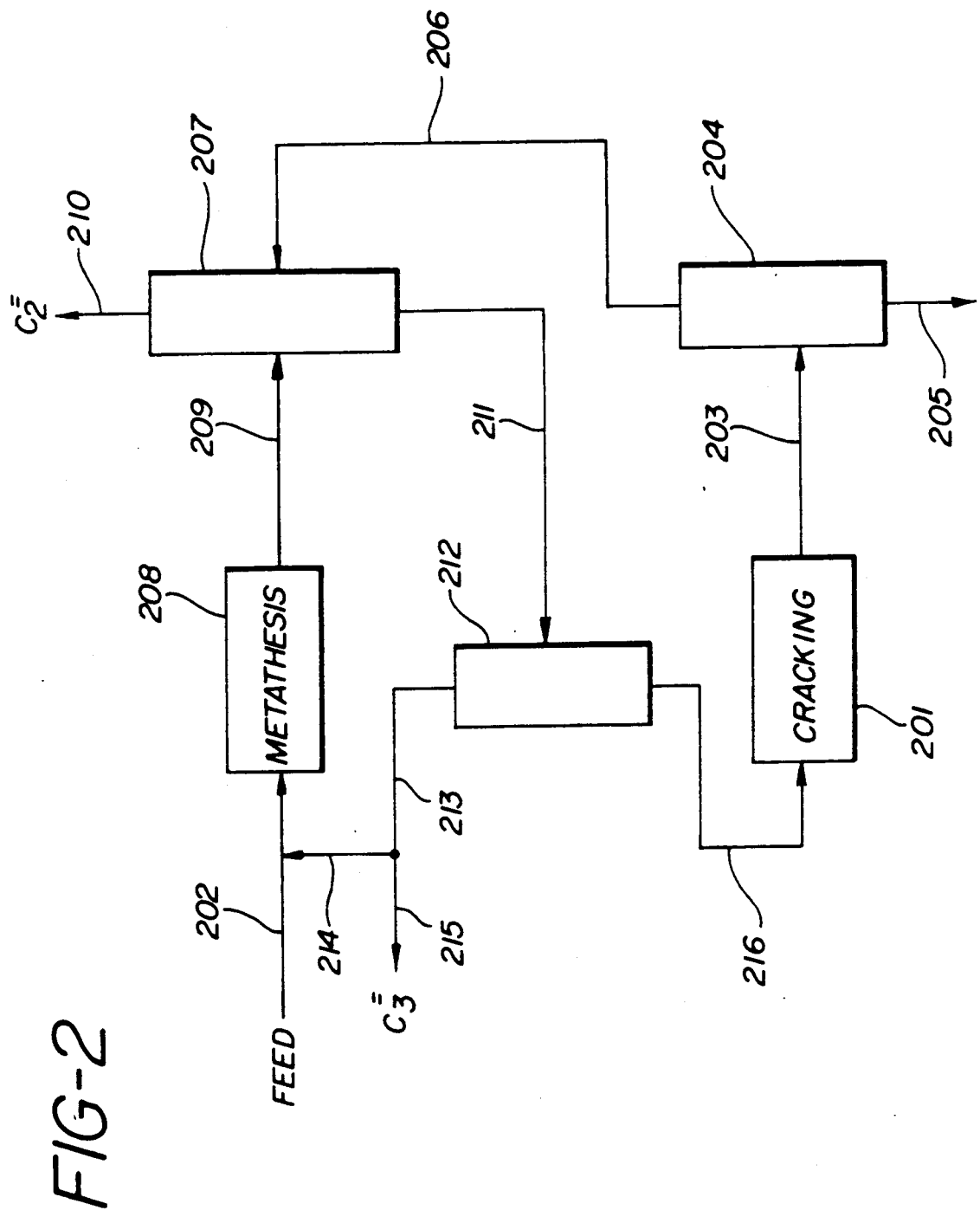

ENHANCED PRODUCTION OF ETHYLENE FROM HIGHER HYDROCARBONS

BACKGROUND OF THE INVENTION

1. Field of the Invention

The present invention provides an improved method for the production of ethylene from a $C_4$ or higher hydrocarbon feed. Specifically, in accordance with the invention, a higher hydrocarbon is converted over a zeolite catalyst at conditions which favor production of a product mixture containing ethylene and propylene. Ethylene is separated from this product mixture and recovered. The propylene from the reaction mixture is metathesized in order to convert the $C_3$ olefin to further quantities of product ethylene as well as higher olefin which latter material can be recycled to the original conversion step.

2. Description of the Prior Art

Ethylene is an important chemical of commerce. In general, ethylene is largely derived from selected petroleum feed materials by procedures such as steam cracking which also produce high quantities of other materials. At times, there exist shortages of ethylene which result in uncertainties in feed supplies, rapidly escalating raw material costs and similar situations which are undesirable from a commercial standpoint. Also, due to imbalances in hydrocarbon values, economics favor using alternate feedstocks provided an effective process for forming ethylene was available.

Methods are known for the conversion of higher hydrocarbons to reaction mixtures comprised of the $C_2$ and $C_3$ lighter olefins. For example, published European patent applications Publication Nos. 0109059 and 0109060 provide illustrative teachings of conditions and catalysts which are effective for the conversion of higher hydrocarbons such as butenes to the lighter olefins. Copending application Ser. No. 07/343097, filed Apr. 25, 1989, likewise provides a comprehensive teaching of prior methods for the production of the lower olefins from higher hydrocarbon feed materials. In certain instances, it would be distinctly advantageous to provide means for still further improving yields of ethylene which result from the conversion of less expensive higher hydrocarbon feed materials.

The disproportionation or metathesis of olefins is likewise a known reaction. In this regard, reference can be made to Banks U.S. Pat. No. 3,261,879, to Banks "Olefin Metathesis Technology and Application," *Applied Industrial Catalysis*, Volume III, Chapter 7, Pages 215, et seq., Leach, Editor (1984). In addition, olefin metathesis reaction and catalysts useful therefor are described in U.S Pat. Nos. 3883606, 3915897, 3952070, 4180524, 4431855, 4499328, 4504694, 4517401 and 4547617.

Despite developments in the art, it remains desirable to provide methods for producing higher yields of ethylene from the less expensive higher hydrocarbon feed materials.

SUMMARY OF THE INVENTION

The present invention provides an improved process for the selective production of ethylene from $C_4$ and higher hydrocarbons, especially from $C_4$ and higher olefins and paraffins. In accordance with the invention, in a first step, the higher hydrocarbon is reacted over a zeolitic type catalyst at conditions selected to produce high yields of ethylene and propylene. Ethylene from this reaction is recovered as a product of the process. In order to enhance ethylene yields, propylene from the zeolite conversion is passed to a metathesis reaction zone wherein it is metathesized to produce further quantities of the desired ethylene product as well as higher olefin, e.g., butene. In an especially preferred embodiment, the propylene is metathesized in ad mixture with butene whereby enhanced production of ethylene is achieved. The ethylene from the metathesis reaction represents a product of the process, and butene or higher hydrocarbons therefrom can conveniently be recycled to the original conversion reaction.

DESCRIPTION OF DRAWINGS

The attached drawings (FIGS. 1 and 2) illustrate in schematic fashion certain practices of the invention.

DETAILED DESCRIPTION OF THE INVENTION

Figure 1:
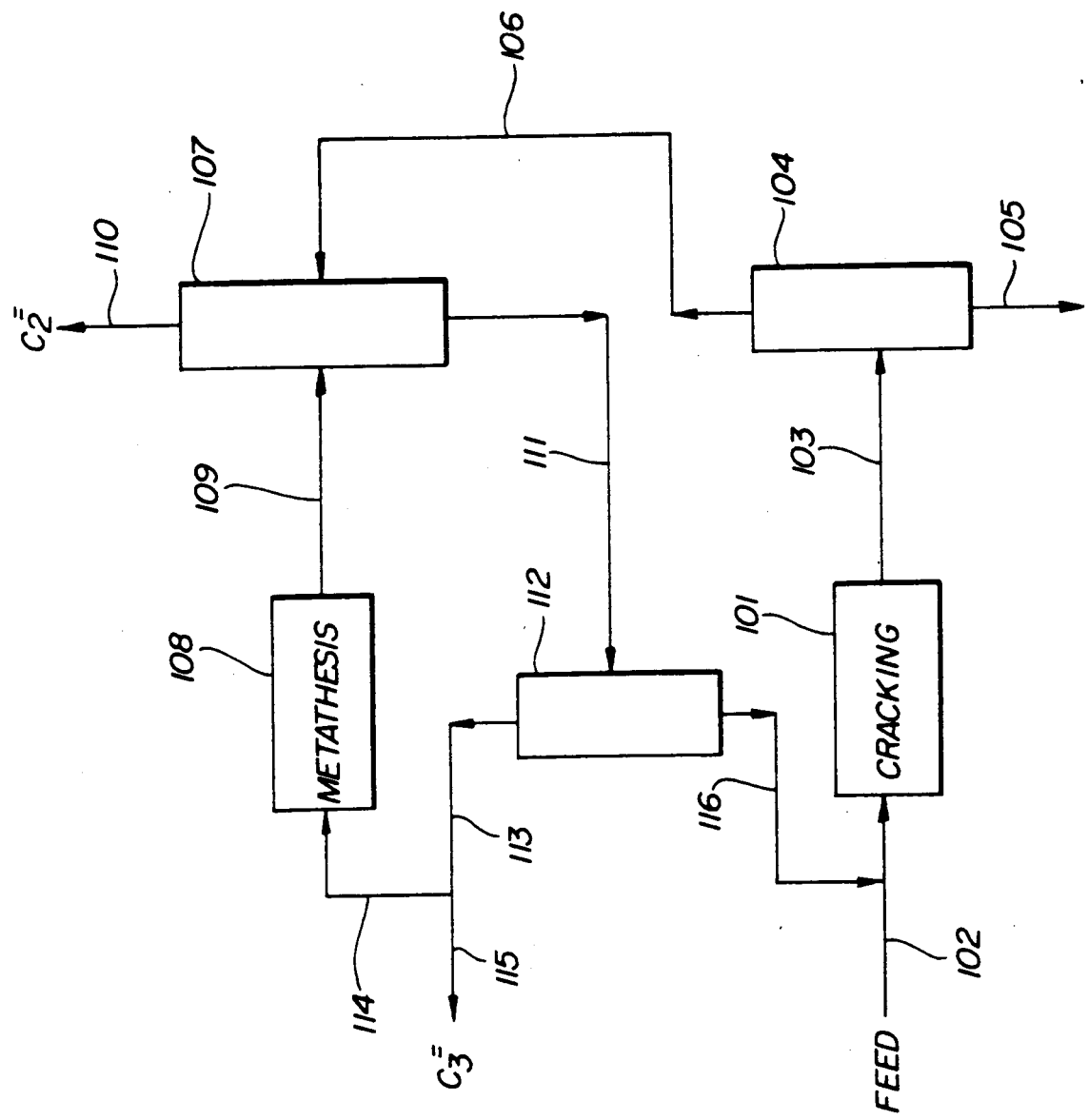

In accordance with the present invention, the higher hydrocarbon feed stock, preferably butenes and/or higher olefins and/or paraffins, is reacted under conditions which favor the production of lower olefins. These conditions generally involve low hydrocarbon partial pressure and high reaction temperatures. The product mixture from this reaction is separated into various components. The ethylene component comprises a product of the process. The propylene component is passed to a metathesis zone alone or in admixture with butene, also contained in the reaction mixture. A heavier component suitable as gasolene blending stock can be recovered.

The propylene metathesis is carried out under conditions and using catalysts which are known in the art. Generally, a catalyst containing a catalytic amount of at least one of molybdenum oxide and tungsten oxide is suitable for the metathesis reaction. Conditions of the metathesis generally include reaction temperature ranging from about 100° to about 450° C., preferably 150° to 350° C., and pressures varying from about atmospheric to upwards of 3,000 psig, although higher pressures can be employed if desired.

Catalysts which are active for the metathesis of olefins and which can be used in the process of this invention are of a generally known type. In this regard, reference is made to "Journal of Molecular Catalysis", 28 (1984) pages 117-131, to "Journal of Catalysis", 13 (1969) pages 99-113, to "Applied Catalysis" 10 (1984) pages 29-229 and to "Catalysis Reviews", 3 (1) (1969) pages 37-60.

Such catalysts may be homogeneous or heterogeneous, with heterogeneous catalysts being preferred. The catalyst preferable comprises a catalytically effective amount of a transition metal component. The preferred transition metals for use in the present invention include tungsten, molybdenum, nickel, rhenium and mixtures thereof. The transition metal component may be present as elemental metal and/or one or more compounds of the metal. If the catalyst is heterogeneous, it is preferred that the transition metal component be associated with a support. Any suitable support material may be employed provided that it does not substantially interfere with the feedstock components or the lower olefin component conversion. Preferably, the support material is an oxide, such as silica, alumina, titania, zirconia and mixtures thereof. Silica is a particularly preferred support material. If a support material is employed, the amount of transition metal component used in combination with the support material may vary widely depending, for example, on the particular application involved and/or the transition metal being used. Preferably, the transition metal comprises about 1% to about 20%, by weight (calculated as elemental metal) of the total catalyst.

The metathesis catalysts advantageously comprise a catalytically effective amount of at least one of the above-noted transition metals, and are capable of promoting olefin metathesis.

Preferably, the metathesis catalyst further comprises at least one activating agent present in an amount to improve the effectiveness of the catalyst. Various activating agents may be employed, including activating agents which are well known in the art to facilitate metathesis reactions. Preferred activating agents include organo-metallic compounds, such as tetra methyl tin, oxides, such as alkaline earth metal oxides, alumina and silica and mixtures thereof. In one particular embodiment, when the activating agent is at least one oxide, the activating agent may be used as a support for the transition metal component. If an organo-metallic activating agent is employed the agent may be included with the catalyst during catalyst preparation, or it may be added during reaction. Preferably, the amount of organo-metallic activating agent is relatively minor compared to the amount of catalytically active metal component in the first catalyst.

The metathesis mixture is resolved by conventional separation means into a product ethylene fraction, a propylene fraction which can be recycled, and a butene and higher hydrocarbon fraction which is preferably recycled to the high hydrocarbon conversion zone for the production of further amounts of ethylene and propylene.

The specified combination of the conversion of the higher hydrocarbons to a mixture comprised of ethylene and propylene at conditions favoring the production of these components coupled with the use of the thus formed propylene to produce further quantities of product ethylene provides a synergistic combination of reaction steps whereby there are obtained substantially improved yields of the desired light olefin, ethylene, from inexpensive and readily available higher hydrocarbon feed materials.

Referring to FIG. 1, the feed hydrocarbon is introduced into cracking zone 101 via line 102. The feed hydrocarbon can be olefinic or paraffinic, or mixtures of olefins and paraffins can be used. $C_4$ and higher feed hydrocarbons are used, examples being butane, the butenes, hexane, hexenes, methyl pentanes, methyl pentenes, cetane, petroleum naphtha fractions and the like.

In zone 101, the hydrocarbon feed, plus any recycle as hereinafter described, is cracked over a zeolitic catalyst such as ZSM-5 at conditions selected to form light olefin product. The conversion is carried out at temperatures in the range of about 400° to 800° C., preferably 500° to 700° C. Low hydrocarbon partial pressures and low conversions per pass favor the lower olefin formation. The hydrocarbon can be admixed with steam or inert gas such as nitrogen. The hydrocarbon partial pressure is as low as practical, illustratively 1 to 30 psia. Where no diluents are employed, system pressures ranging from about $-12$ to 50 psig preferably $-5$ to 30 psig are suitable. Higher pressures can be used when diluents are employed.

High space velocity and short residence times are preferred in order to maintain the desired low conversions per pass. Space velocities are 1 to 5000, preferably 5 to 2000 hr.$^{-1}$ WHSV.

Fixed bed reactions can be used, but fluidized solid procedures are preferred.

Zeolite catalysts used in the invention can be silaceous, crystalline molecular sieves. Such silica-containing crystalline materials include materials which contain, in addition to silica significant amounts of alumina. These crystalline materials are frequently named "zeolites, i.e., crystalline aluminosilicates." Silica-containing crystalline materials also include essentially aluminum-free silicates. These crystalline materials are exemplified by crystalline silica polymorphs (e.g. silicalite, disclosed in U.S. Pat. No. 4,061,724 and organosilicates, disclosed in U.S. Pat. Re. No. 29948), chromia silicates (e.g., CZM) ferrosilicates and galliosilicates (see U.S. Pat. No. 4,238,318), and borosilicates (see U.S. Pat. No. 4,226 420; 4 269 813; and 4,327,236).

Crystalline aluminosilicate zeolites are best exemplified by ZSM-5 (see U.S. Pat. Nos. 3,702,886 and 3,770,614), ZSM-11 (see U.S. Pat. No. 3,709,979), ZSM-12 (see U.S. Pat. No. 3,832,449), ZSM-21 and ZSM-38 (see U.S. Pat. No. 3,948,758), ZSM-23 (see U.S. Pat. No. 4,076,842), and ZSM-35 (see U.S. Pat. No. 4,016,246).

Acid aeolites are especially preferred, particularly the ZSM type and borosilicates. ZSM-5 is especially useful.

Phosphorous containing zeolites such as are described in U.S. Pat. No. 3,972,832 are also especially useful.

In addition to the above, zeolite-containing materials can be used. Representative of such materials are zeolite A (U.S. Pat. No. 2,882,243), zeolite X (U.S. Pat. No. 2,882,244), zeolite Y (U.S. Pat. No. 3,130,007), zeolite ZK-5 (U.S. Pat. No. 3,247,195), zeolite ZK-4 (U.S. Pat. No. 3,314,752), synthetic mordenite, and dealuminized mordenite as well as naturally occurring zeolites, including chabazite, faujasite, mordenite and the like.

In general, the zeolites are ordinarily ion-exchanged with a desired cation to replace alkali metal present in the zeolite as found naturally or as synthetically prepared. The exchange treatment is such as to reduce the alkali metal content of the final catalyst to less than about 0.5 weight percent. Preferred exchanging cations are hydrogen, ammonium, rare earth metals and mixtures thereof, with particular preference being accorded rare earth metals. Ion exchange is suitably accomplished by conventional contact of the zeolite with a suitable salt solution of the desired cation, such as, for example, the sulfate, chloride or nitrate salts.

It is preferred to have the crystalline zeolite of a suitable matrix, since the catalyst form is generally characterized by a high resistance to attrition, high activity and exceptional steam stability. Such catalysts are readily prepared by dispersing the crystalline zeolite in a suitable siliceous sol and gelling the sol by various means. The inorganic oxide which serves as the matrix in which the above crystalline zeolite is distributed includes silica gel or a cogel of silica and a suitable metal oxide. Representative cogels include silica-aluminia silica-magnesia, silica-zirconia, silica-thoria, silica-beryllia, silica-titania as well as ternary combinations, such as silica-alumina-magnesia, silica-aluminia-zirconia and silica-magnesia-sirconia. Preferred cogels include silica-alumina, silica-zirconia or silica-alumina-zirconia. The above gels and cogels will generally comprise a major proportion of silica and a minor proportion of the other aforementioned oxide or oxides. Thus, the silica content of the siliceous gel or cogel matrix will generally fall within the range of 55 to 100 weight percent, preferably 60 to 95 weight percent, and the other metal oxide or oxides content will generally be within the range of 0 to 45 weight percent. In addition to the above, the matrix may also comprise natural or synthetic clays, such as kaoline type clays, montmorillonite, bentonite or halloysite. These clays may be used either alone or in combination with silica or any of the above specified cogels in a matrix formulation.

From zone 101, the reaction mixture passes via line 103 to separation zone 104.

A heavy purge stream is removed from zone 104 via line 105. The bulk of the products from cracking zone 101 including the ethylene and propylene passes via line 106 to separation zone 107. An ethylene-containing stream from metathesis zone 108 passes to zone 107 via line 109. In zone 107, product ethylene is recovered overhead via line 110. Higher boiling compounds pass via line 111 to separation zone 112 wherein the higher boiling compounds are further separated by distillation.

Propylene is removed overhead via line 113; at least a portion of the propylene passes via lines 113 and 114 to metathesis zone 108 wherein the propylene is metathesized to ethylene and butene, and the metathesis product mixture is then passed via line 109 to separation zone 107 as described above.

A propylene product stream can be recovered via line 115.

Hydrocarbons boiling higher than propylene pass from separation zone 112 via line 116 to join the feed hydrocarbon which is introduced via line 102 and the mixture passes to cracking zone 101 wherein, as described above, the mixture contacts the zeolitic catalyst under conditions at which ethylene and propylene production is favored.

A somewhat different embodiment of the invention is described in FIG. 2. In this embodiment, feed hydrocarbon comprising isobutylene is introduced via line 202 into metathesis zone 208 wherein it is admixed with propylene introduced via line 213, and the mixture is metathesized to form ethylene and $C_5$ olefin.

The metathesis mixture passes via line 209 to distillation zone 207. Also introduced into distillation zone 207 via line 206 is a stream from separation zone 204 which contains both ethylene and propylene.

Product ethylene is removed overhead from zone 207 via line 210. Higher boiling materials pass via line 211 to distillation zone 212. Propylene is removed overhead via line 213 and at least a portion thereof passes to metathesis zone 208 for conversion to ethylene as above described. A portion of the propylene can be recovered as product via line 215.

$C_4$ and higher components pass from zone 212 via line 216 to cracking zone 201 wherein they are reacted over a zeolitic catalyst at conditions such that ethylene and propylene are formed.

The cracking reaction mixture passes via line 203 to separation zone 204 from which a heavier material purge is removed via line 205. The lighter fraction comprised of ethylene and propylene formed in the cracking reaction passes via line 206 to separation zone 207 as described above.

Ethylene yields as high as 36% based on the carbon content of the hydrocarbon feed can be achieved. Reaction conditions, catalysts and the like are conventional and require no extraordinary catalysts, materials or construction and the like.

The following examples, with special reference to the attached drawings, serve to more fully illustrate practice of the invention.

EXAMPLE 1

Referring to FIG. 1, isobutylene feed in amount of 101 mols per hour is fed via line 102 to cracking zone 101. Combined with the isobutylene is a stream from separation zone 112 passing via line 116 to line 102 and thence to zone 101. The stream in line 116 consists of $C_4$ and higher hydrocarbons in amount of 202.9 mols per hour.

The combined hydrocarbons mixture is contacted with a ZSM-5 catalyst in zone 101. Temperature is 600° C. and space velocity is 10 hr.$^{-1}$ WHSV. Conditions in zone 101 favor the formation of lower olefins.

The reaction mixture from zone 101 containing ethylene and propylene passes via line 103 to separation zone 104; a heavies purge in amount of 15.7 mols per hour is separated via line 105.

The remainder of the reaction product mixture passes via line 106 to separation zone 107 for separation of product ethylene. Also introduced into zone 107 is an ethylene-containing stream from metathesis zone 108 which passes to zone 107 via line 109.

By conventional distillation procedures, a product ethylene stream is removed overhead from zone 107 via line 110 at the rate of 72.5 mols per hour.

The materials which are higher boiling than ethylene, comprised of propylene and higher hydrocarbons pass via line 111 to separation zone 112 wherein by conventional distillation a propylene stream is separated overhead at the rate of 210.6 mols per hour via line 113 from higher boiling materials.

About 60.6 mols per hour of the propylene is recovered via line 115 and represents a product of the process. About 150 mols per hour of propylene passes via line 114 to metathesis zone 108 for conversion to an ethylene-containing metathesis reaction product mixture.

In zone 108, the propylene is contacted at metathesis conditions with a metathesis catalyst comprised of $WO_3$ supported on silica; temperature is 350° C. and space velocity is 15 hr.$^{-1}$ WHSV.

The metathesis product mixture passes via line 109 to separation zone 107 for recovery of ethylene and recycle of higher materials as above described.

The heavy fraction from zone 112 passes at the rate of 202.9 mols per hour via line 116 where it is combined with fresh isobutylene via line 102 and these materials are cracked in zone 101 as above described to form the desired lower olefin product mixture.

The compositions of the various process and product streams expressed in mols per hour is given in the following Table 1.

TABLE 1

| Stream | MOLS PER HOUR | | | | | | | | | |
|---|---|---|---|---|---|---|---|---|---|---|
| | 102 | 114 | 109 | 106 | 110 | 111 | 115 | 116 | 103 | 105 |
| Component | | | | | | | | | | |

TABLE 1-continued

| Stream | MOLS PER HOUR | | | | | | | | | |
|---|---|---|---|---|---|---|---|---|---|---|
| | 102 | 114 | 109 | 106 | 110 | 111 | 115 | 116 | 103 | 105 |
| $C_2=$ | | | 33.9 | 38.6 | 72.5 | | | | 36.8 | |
| $C_3=$ | | 150.0 | 82.2 | 128.2 | | 250.3 | 60.6 | | 128.2 | |
| $iC_4=$ | 101.0 | | | 18.0 | | 18.0 | | 18.0 | 19.4 | 1.4 |
| $nC_4=$ | | | 33.9 | 34.0 | | 67.9 | | 67.9 | 36.6 | 2.6 |
| Paraffin $C_4$ | | | | 17.0 | | 17.0 | | 17.0 | 18.7 | 1.7 |
| olefin $C_5+$ | | | | 30.0 | | 30.0 | | 30.0 | 33.0 | 3.0 |
| P/A* $C_5+$ | | | | 70.0 | | 70.0 | | 70.0 | 77.0 | 7.0 |
| TOTAL | 101.0 | 150.0 | 150.0 | 335.8 | 72.5 | 453.2 | 60.6 | 202.9 | 351.5 | 15.7 |

*paraffin/aromatic

EXAMPLE 2

Referring to FIG. 2, isobutylene feed in amount of 100 mols per hour is fed via line 202. A recycle propylene stream in amount of 115 mols per hour fed via line 214 is combined with the isobutylene feed, and this mixture is fed to metathesis zone 208 wherein the propylene and isobutylene are metathesized to form ethylene and $C_5$ olefin. The metathesis conditions include a temperature of about 400° C. and a space velocity of about 30 hr.$^{-1}$ WHSV. The catalyst employed in the metathesis is $WO_3$ supported on silica. From zone 208, reaction mixture passes via line 209 to separation zone 207 where it is combined with a stream containing ethylene and propylene formed in cracking zone 201 as hereinafter described.

Separation zone 207 operates in accordance with conventional distillation procedures and an overhead product ethylene stream in amount of 72.5 mols per hour is recovered via line 210.

Components which are higher boiling than ethylene pass from zone 207 by means of line 211 to separation zone 212. In zone 212, again by conventional distillation procedures, propylene is removed via line 213 as an overhead product steam. A portion of this propylene, 115 mols per hour, passes via line 214 for combination with the feed isobutylene as above described, and this mixture is metathesized in zone 208. A product propylene stream in amount of 60.6 mols per hour is recovered by means of line 215. Materials which are higher boiling than propylene pass from separation zone 212 via line 216 to cracking zone 201. In zone 201, these higher hydrocarbons are contacted with ZSM-5 catalysts at cracking conditions which favor the formation of ethylene and propylene. Specifically, a temperature of 650° C. and a space velocity of 15 hr.$^{-1}$ WHSV is employed. Pressure in the cracking zone is 5 psig.

The reaction mixture resulting from this cracking passes via line 203 to separation Zone 204, and a heavier purge stream in amount of 14.3 mols per hour is removed via line 205. Overhead from separation zone 204 containing the ethylene and propylene formed in zone 201 passes via line 206 to separation zone 207 wherein it is distilled together with the metathesis reaction mixture and product ethylene is recovered as above described.

The compositions of the various process and product streams expressed in mols per hour are given in the following Table 2.

TABLE 2

| Stream | MOLS PER HOUR | | | | | | | | | |
|---|---|---|---|---|---|---|---|---|---|---|
| | 202 | 214 | 209 | 206 | 210 | 211 | 215 | 216 | 203 | 205 |
| Component | | | | | | | | | | |
| $C_2=$ | | | 41.0 | 31.5 | 72.5 | | | | 31.5 | |
| $C_3=$ | | 115.0 | 59.0 | 116.6 | | 175.6 | 60.6 | | 116.6 | |
| $iC_4=$ | 100.0 | | | 24.3 | | 24.3 | | 24.3 | 25.4 | 1.1 |
| $nC_4=$ | | | 88.0 | 50.2 | | 138.2 | | 138.2 | 52.6 | 2.4 |
| Paraffin $C_4$ | | | | 13.0 | | 13.0 | | 13.0 | 14.3 | 1.3 |
| olefin $C_5+$ | | | 27.0 | 67.0 | | 94.0 | | 94.0 | 70.5 | 3.5 |
| P/A* $C_5+$ | | | | 58.0 | | 58.0 | | 58.0 | 64.0 | 6.0 |
| TOTAL | 100.0 | 115.0 | 215.0 | 360.6 | 72.5 | 503.1 | 60.6 | 327.5 | 374.9 | 14.3 |

*paraffin/aromatic

What is claimed is:

1. The method for the production of ethylene which comprises:
   (a) cracking a $C_4$ or higher hydrocarbon over a zeolite catalyst at conditions favoring production of ethylene and propylene to form a mixture comprised of ethylene, propylene and butene,
   (b) recovering ethylene from the step (a) reaction mixture,
   (c) metathesizing propylene from the step (a) reaction mixture to form additional ethylene together with butene,
   (d) recovering said additional ethylene from the step (c) reaction mixture, and
   (e) recycling butene contained in the mixture from step (a) and formed in step (c) to the cracking reaction of step (a).

2. The method of claim 1 wherein a mixture of propylene and butene is metathesized in step (c).

* * * * *